United States Patent [19]

Jennings

[11] 4,269,830
[45] May 26, 1981

[54] COMPOSITIONS AND METHODS FOR THE TREATMENT OF CHRONIC TRYPANOSOMIASIS INFECTIONS

[75] Inventor: Francis W. Jennings, Glasgow, Scotland

[73] Assignee: Merck & Co., Inc., Rahway, N.J.

[21] Appl. No.: 39,706

[22] Filed: May 17, 1979

[51] Int. Cl.$^3$ .................... A61K 31/655; A61K 31/42
[52] U.S. Cl. ...................................... 424/226; 424/272
[58] Field of Search ................................ 424/272, 226

[56] References Cited

U.S. PATENT DOCUMENTS

| 3,646,027 | 2/1972 | Carlson et al. | 424/273 |
|---|---|---|---|
| 3,711,495 | 1/1973 | Kulsa et al. | 424/272 |
| 3,737,547 | 6/1973 | Carlson et al. | 424/273 |
| 3,915,978 | 10/1975 | Kulsa et al. | 424/272 |
| 4,010,176 | 3/1977 | Kulsa et al. | 424/272 |

OTHER PUBLICATIONS

Jennings et al., Parasitology, vol. 75, pp. 143-153 (1977).
Cuckler, Am. J. of Tropical Med. and Hygiene, vol. 19, pp. 916-925 (1970).
Beaman et al., Antimicrobial Agents and Chemotherapy, pp. 520-530 (1967).
Neville et al., J. of Med. Chem., vol. 20, pp. 946-949 (1977).
Bailey, Trans. Roy. Soc. Trop. Med. and Hyg., vol. 62, p. 122 (1968).
The Merck Index, 9th Ed., Merck & Co., Inc., Rahway, N. J., 1976, pp. 434-435.

*Primary Examiner*—Jerome D. Goldberg
*Attorney, Agent, or Firm*—David L. Rose; Harry E. Westlake

[57] ABSTRACT

Compositions comprising substituted 5-nitroimidazoles and diminazene aceturate (Berenil) useful in the treatment of chronic trypanosomiasis infections in humans and animals. The substituted 2- or 5-nitroimidazoles having a 1-alkyl substituent and a 2-substituent, the latter being a $\Delta^2$-4',5'-disubstituted isoxazoline. The 4',5'-substitution on the isoxazoline moiety is a saturated alkyl ring. Method of treatment of chronic trypanosomiasis infections in humans and animals by administering said compositions.

3 Claims, No Drawings

COMPOSITIONS AND METHODS FOR THE TREATMENT OF CHRONIC TRYPANOSOMIASIS INFECTIONS

BACKGROUND OF THE INVENTION

Trypanosomiasis is a term used to describe a group of allied protozoal diseases, each of which is due to infection with a species of the genus Trypanosoma. They reach great importance in Africa where their presence in enzootic form precludes the keeping of domestic animals throughout the largest part of the continent between 15°N and 20°S latitude. The pathogenic trypanosomes of Africa are considered to be primarily associated with the tsetse flies (glossina) which feed on vertebrate blood. The tsetse is the vector and also is the host in which part of the trypanosome life cycle takes part. Wherever tsetse are present, trypanosomiasis will also be found in some part of the mammalian population. The clinical findings are typically those of a wasting disease with intermittent fever. Anemia, edema, and cachexia are parts of the syndrome.

The important trypanosomes pathogenic to domestic animals are *T. congolense, T. vivax, T. simiae, T. suis, T. equiperdum,* and *T. brucei.* The latter trypanosome is morphologically identical to *T. gambiense,* and *T. rhodesiense,* responsible for human "sleeping sickness" of Africa. The tsetse fly is the vector in the transmittal of these trypanosomes. The trypanosomes *T. evansi* and *T. vivax* are also mechanically transmitted by bloodfeeding insects. One trypanosome found in the Western Hemisphere is *T. cruzi,* which infects both animals and man and in man causes a very serious condition known as Chagas' disease.

Acute Chagas' disease (*T. cruzi*) occurs in people of all ages but is especially important in the adolescent. The chronic form may be mild and asymptomatic, although it frequently gives rise to myocarditis and N.S. (nervous system) involvement resulting in morbidity and premature mortality.

A recurring problem in the chemotherapy of trypanosomiasis is the patient or animal which relapses after treatment. If the drug fails to clear the circulating parasitaemia or if the parasites reappear in the bloodstream after an aparasitaemic phase which varies depending on the persistence and level of the drugs used, then there is a distinct possibility that either underdosage of the drug is the causative factor or drug resistance has occurred. If, however, there is a prolonged aparasitaemic phase after chemotherapy before the eventual reappearance of the parasite this, in many instances, has been attributed to reinfection if the animal has remained in the endemic area. The other possibility is the existence of an "occult" phase of the disease, which gives rise to a new cycle of parasitaemia.

This was described in greater detail in the case of *T. brucei* TREU 667/1 infection in the mouse by Jennings, Whitelaw and Urquhart, *Parasitol.* 75, 143–153 (1977), who found that infections of mice with this stabilate could be cured permanently if treatment was initiated early in the infection (3–7 days) but that if it were delayed (14–21 days), then nearly all the mice eventually relapsed despite the mice being treated with many times the recommended dose of drugs.

BRIEF SUMMARY OF INVENTION

The present invention is directed to novel compositions and methods for the treatment of chronic trypanosomiasis infections. Said compositions comprise substituted 2- or 5-nitroimidazoles and diminazene aceturate (Berenil). Said substituted 2- or 5-nitroimidazoles included in the novel compositions are those showing trypanosomal activity described in U.S. Pat. Nos. 3,711,495, 3,915,978 and 4,010,176. Preferred 5-nitroimidazoles, described in U.S. Pat. No. 3,711,495, are those having a 1-loweralkyl substituent of 1 to 6 carbon atoms and a 2-substituent which is a Δ²-isoxazoline fused at the 4',5'-position to a 6 or 8 membered saturated alkyl ring. Further preferred 5-nitroimidazoles are those described in U.S. Pat. No. 3,646,027, and U.S. Pat. No. 3,737,547. Further preferred nitroimidazoles useful in the present novel compositions are set forth below:

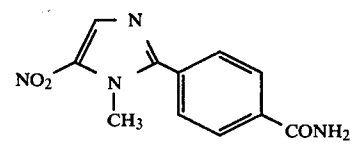

Cuckler et al., Amer. J. Trop. Med. Hyg., 19, 916 (1970)

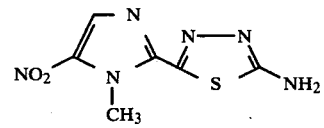

Burden, Antimicrob. Agents and Chemotherapy p.545 (1968).

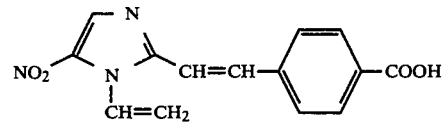

Ross et al., J. Med. Chem., 15, 1035(1972) and 16, 347(1973).

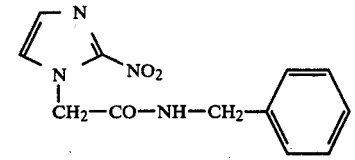

Antimicrobial Agents and Chemtherapy, p.520(1967)

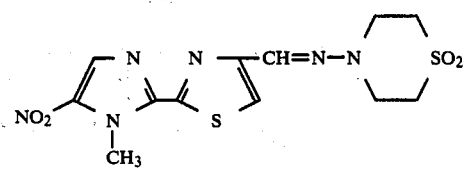

J. Med. Chem., 20, 946(1977)

It is contemplated that those nitroimidazoles described above having trypanosomal activity may equally well be incorporated in the present novel Berenil-nitroimidazole compositions to provide compositions useful for the treatment of relapsing trypanosomiasis.

The following non-limiting Examples will serve to further illustrate the instant invention.

MATERIALS AND ASSAY METHODS

The mice used were adult CFLP females approximately 25–30 g. and maintained on standard laboratory diet throughout the experiments.

Two stabilates were used throughout the experiments, the main one was *T. brucei* TREU 667/1 originally obtained from Dr. A. R. Gray, Edinburgh, and the other *T. brucei* LUMP 1001 obtained from Professor W. H. R. Lumsden, London. These were cryogenically maintained as previously described in Jennings, Whitelaw and Urquhart, *Parasitol.* 75, 143-153 (1977).

Each mouse was inoculated introperitoneally with $1 \times 10^4$ trypanosomes prepared from the stabilate in phosphate glucose saline pH 8.0. Chemotherapy commenced at various times post inoculation. Each mouse was weighed and the requisite dose of drug administered intraperitoneally in a volume of 0.1 ml./5 g. body weight.

The nitroimidazoles tested were:

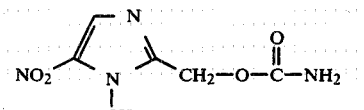

I. 1-methyl-5-nitroimidazol-2-ylmethylcarbamate

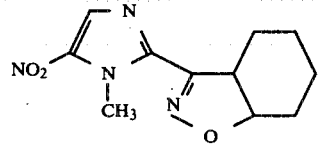

II. 3'-(1-methyl-5-nitroimidazol-2-yl)-4'5'-tetramethylene-$\Delta^2$-isoxazoline

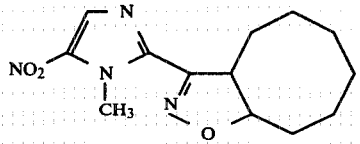

III. 3'-(1-methyl-5-nitroimidazol-2-yl)-4',5'-hexamethylene-$\Delta^2$-isoxazoline Hereinafter, the above named Compounds are referred to by their designated Roman numerals.

Compounds I, II and III were used in crystalline powder forms. These were first ground finely in an agate mortar and then suspended in physiological saline for intraperitoneal injection. A drop of detergent (Tween 80) was added to the suspensions to facilitate wetting. Care was taken during dispensing that the suspensions were properly dispersed, and because of some slight unavoidable settlement in the syringe, the mice were always injected at random and usually not more than 3 mice were injected from the one syringe full of drug suspension. As the regimen was usually 4 daily doses at the respective drug concentration, any errors were evenly distributed.

The other established drugs used were Berenil (diminazene aceturate, obtained from Fabwerke, Hoechst, Germany, 40 mg./kg. unless otherwise specified), Ethidium (homidium bromide 7.5 mg./kg.) and Prothidium (pyrithidium bromide 10 mg./kg. obtained from Boots Pure Drug Co., England) and Samorin (isometamidium 2 mg./kg. obtained from May & Baker Ltd.). All were prepared according to the manufacturer's instructions and were injected intraperitoneally.

The mice were examined for parasites on the day treatment was initiated (usually day 3 or 21 of infection) by examination of a drop of tail blood under ×40 objective (wet film technique). Subsequent to treatment they were examined every 2 days for 6 days and thereafter once per week until relapse occurred or until the experiment was terminated (in some instances 6–7 months).

The mice which showed relapse parasitaemias were removed from their experimental groups to a separate holding cage after they showed a positive wet blood film on two separate occasions.

EXAMPLE 1

The Effect of Compounds I, II and III on Early Infections of *T. brucei* TREU 667/1

The three compounds, I, II and III were used at various dose levels against an early infection of *T. brucei* TREU 667/1 in CFLP. The dose regimen was initiated 3 days after infection and the intraperitoneal injections of drug suspension were given daily. The results are set forth in Table 1:

TABLE 1

Effectiveness of Compounds I, II and III When Administered to Mice Infected For 3 Days With *Trypanosoma brucei* TREU 667/1

| Drug | Number and Level of Daily Doses | Number Cured≠ Out of Total Treated |
|---|---|---|
| I | 4 × 5 mg./kg. | 0/8 |
|   | 4 × 20 mg./kg. | 0/8 |
| II | 4 × 5 mg./kg. | 0/8 |
|   | 4 × 20 mg./kg. | 2/8 |
| II** | 4 × 80 mg./kg. | 10/10 |
| III | 4 × 5 mg./kg. | 2/8 |
|   | 4 × 20 mg./kg. | 8/8 |

**Separate experiment
≠Cure indicates that relapses did not occur, i.e., that there was a complete absence of parasites in the blood for at least 90 days after treatment or till the end of the experiment.

The initial results (Table 1) using dose regimens of 4 daily doses at 5 and 20 mg./kg. of Compound I did not result in any cures. Compound III, 4 doses at 20 mg./kg. gave 100% cure of a 3-day old infection. There was some indication of activity with Compound II administered in 4 doses of 20 mg./kg. and for that reason the experiment was repeated using 4 doses of 80 mg./kg. which also gave a 100% cure rate.

EXAMPLE 2

The Effect of Compounds II and III Alone and in Combination Against Chronic Infections of *T. brucei* TREU 667/1

The Compounds II and III which showed promise against 3 day old infections in Example 1 were tested against 21 day old infections of *T. brucei* TREU 667/1 which previous work had shown relapsed after treatment at this time after infection with many of the conventional drugs alone (Berenil, Ethidium, Prothidium, Samorin) even when used at many times the dose rate effective against early infections. Compounds II and III were used singly and in various combinations and the results are shown in Table 2:

TABLE 2

Effectiveness of Compounds II and III Alone and in Combination When Administered to Mice Infected for 21 Days With *Trypanosoma brucei* TREU 667/1

| Drug | Number and Level of Daily Doses | Number Cured≠ Out of Total Treated |
|---|---|---|
| III | 4 × 20 mg./kg. | 0/9 |
|   | 4 × 20 mg./kg. | 0/10 |
|   | 4 × 80 mg./kg. | 0/10 |
| III* | 4 × 20 mg./kg. | 0/8 |
| II* | 4 × 20 mg./kg. | 0/9 |
| II+ | Simultaneously |   |
| III* | 4 × 20 mg./kg. each | 1/10 |

TABLE 2-continued

Effectiveness of Compounds II and III Alone and in Combination When Administered to Mice Infected for 21 Days With *Trypanosoma brucei* TREU 667/1

| Drug | Number and Level of Daily Doses | Number Cured≠ Out of Total Treated |
|---|---|---|
| II+ III* | 4 × 20 mg./kg. II followed by 4 × 20 mg./kg. III | 1/10 |
| III+ II* | 4 × 20 mg./kg. III followed by 4 × 20 mg./kg. II | 1/10 |

*Constituted single experiment
≠Cure indicates that relapses did not occur, i.e., that there was a complete absence of parasites in the blood for at least 90 days after treatment or till the end of the experiment.

In every instance the Compounds II and III used, either singly or in various combination, failed to cure the 21 day old infections of *T. brucei* TREU 667/1 in that relapses occurred from 5 days onward.

EXAMPLE 3

The Effect of Treatment with Other Trypanocidal Drugs Alone and In Combination on Chronic Infections of *T. brucei* TREU 667/1

The effect of pre-treatment on infection of *T. brucei* TREU 667/1 established for 21 days with the three established drugs Ethidium, Prothidium and Samorin is shown in Table 3. Pre-treatment of a 21 day old infection of *T. brucei* TREU 667/1 with Ethidium at 7.5 mg./kg. followed by Compound III at day 24 either in the form of one dose at 80 mg./kg. or 4 doses of 20 mg./kg. each had no effect since the infection subsequently relapsed. The results are set forth in Table 3:

TABLE 3

The Effect of Pretreatment With Ethidium, Prothidium or Samorin on the Efficacy of Compound III on a 21 Day Old Infection of *Trypanosoma brucei* TREU 667/1

| Pretreatment Day 21 | | Treatment Commencing Day 24 | | No. Cured≠ Out of Total Treated |
|---|---|---|---|---|
| Drug | Dosage | Drug | Number and Level of Daily Doses | |
| Ethidium | 7.5 mg./kg. | — | — | 0/10 |
| Ethidium | 7.5 mg./kg. | III | 4 × 20 mg./kg. | 0/10 |
| Ethidium | 7.5 mg./kg. | III | 1 × 80 mg./kg. | 0/7 |
| Prothidium | 10.0 mg./kg. | — | — | 0/8 |
| Prothidium | 10.0 mg./kg. | III | 4 × 20 mg./kg. | 3/7 |
| Prothidium | 10.0 mg./kg. | III | 1 × 80 mg./kg. | 4/8 |
| Samorin | 2.0 mg./kg. | — | — | 0/10 |
| Samorin | 2.0 mg./kg. | III | 4 × 20 mg./kg. | 0/10 |
| Samorin | 2.0 mg./kg. | III | 1 × 80 mg./kg. | 5/7 |
| — | — | III | 4 × 20 mg./kg. | 0/8 |

≠Cure indicates that relapses did not occur, i.e., that there was a complete absence of parasites in the blood for at least 90 days after treatment or till the end of the experiment.

EXAMPLE 4

The Effect of Treatment with Berenil Alone and In Combination With Compound III on Chronic *T. brucei* TREU 667/1 Infections The initial work with Berenil was carried out using the dose rate of 40 mg/kg. which was the dose of drug used in all the original work on chronic infections.

TABLE 4

The Effect of Treatment with Berenil Alone and in Combination With Compound III on a 21 Day-old Infection of *Trypanosoma brucei* TREU 667/1

| Pretreatment Day 21 | | Treatment Commencing Day 24 | | No. Cured≠ Out of Total Treated |
|---|---|---|---|---|
| Drug | Dose | Drug | Number and Level of Daily Doses | |
| Berenil | 5 mg./kg. | — | — | 0/10 |
| Berenil | 5 mg./kg. | Berenil | 5 mg./kg. | 0/10 |
| Berenil | 5 mg./kg. | III | 4 × 20 mg./kg. | 0/9 |
| Berenil | 5 mg./kg. | III | 4 × 80 mg./kg. | 0/10 |
| Berenil | 5 mg./kg. | III | 1 × 20 mg./kg. | 0/10 |
| Berenil | 5 mg./kg. | III | 1 × 80 mg./kg. | 0/10 |
| Berenil | 20 mg./kg. | — | — | 0/10 |
| Berenil | 20 mg./kg. | III II | 4 × 20 mg./kg. each drug | 4/10 |
| Berenil | 40 mg./kg. | — | — | 1/10 |
| Berenil | 40 mg./kg. | — | — | 1/9 |
| Berenil | 40 mg./kg. | III | 4 × 20 mg./kg. | 9/10 |
| Berenil | 40 mg./kg. | III | 1 × 80 mg./kg. | 9/10 |
| Berenil | 40 mg./kg. | III | 4 × 20 mg./kg. | 9/10 |
| Berenil | 40 mg./kg. | — | — | 6/10 |
| Berenil | 40 mg./kg. | III | 4 × 20 mg./kg. | 8/10* |
| Berenil | 40 mg./kg. | III | 1 × 80 mg./kg. | 10/10 |
| Berenil + III | 40 mg./kg. 80 mg./kg. | — | — | 10/10 |

≠Cure indicates that relapses did not occur, i.e., that there was a complete absence of parasites in the blood for at least 90 days after treatment or until the end of the experiment.
*2 mice died shortly after treatment regimen - no signs of trypanosomes.

In addition, groups of mice were given Berenil and the Compound III simultaneously, or one injection of Berenil followed by one injection of Compound III in order to compress the treatment into the minimum number of injections. The results are set forth in Table 4.

The results showed that if Berenil is administered at 40 mg./kg. followed by Compound III usually administered 3 days after the Berenil either as a single dose (1×80 mg.) or 4 doses of 20 mg./kg. then the successful permanent cures were between 90–100%. In one experiment there was an exceptionally high number 6/10 of the mice receiving the Berenil (40 mg./kg.) alone, which were apparently permanently cured, usually this is around 1%.

It was also apparent that pre-treatment with Berenil at lower dose levels was not effective in preventing relapses, although 20 mg./kg. Berenil followed by a combination of the two Compounds III and II each at 20 mg./kg. (4 doses) cured 4/10 mice.

The simultaneous administration of Berenil (40 mg./kg.) and Compound III (80 mg./.kg.) also seemed highly effective (100%) until judged against the 6/10 (60%) cure rate for Berenil (40 mg./kg.) given alone in that particular experiment. In all experiments, there seemed little advantage in administering Compound III in 4 doses (4×20 mg./kg.) rather than as a single dose (1×80 mg./kg.).

EXAMPLE 5

The Effect of Treatment With Berenil Alone and In Combination With Compound III on Chronic *T. brucei* LUMP 1001 Infections In order to demonstrate that pre-treatment with Berenil followed by Compound III was effective against different isolates of *T. brucei*, the stabilate *T. brucei* LUMP 1001 was used to establish the infections. It was known that *T. brucei* LUMP 1001 relapsed after treatment of a 21 day old infection Jennings, Whitelaw, Urquart, *Parasitol.* 75, 143–153 (1977), and indeed tended to relapse earlier after treatment with Berenil at 40 mg./kg. than any of the other stabilates tested (approximately 20 days). The original experiment using 40 mg./kg. Berenil as pre-treatment followed by Compound III was disappointing, as only 3 out of a total of 27 mice appeared to be cured by the various dose regimens. The experiment was therefore repeated increasing the pretreatment dose of Berenil to 60 mg./kg. and 80 mg./kg., the latter being given as two doses of 40 mg./kg. on consecutive days to avoid the possibility of deaths due to the toxicity of Berenil at that dose level in mice. This pretreatment was followed by administration of Compound III at 4 doses of 80 mg./kg. and in both instances where the increased Berenil dose level (60 mg./kg. and 80 mg./kg.) was used, satisfactory permanent cures were accomplished, whereas in the respective controls all of the mice relapsed. The results are set forth in Table 5:

TABLE 5

The Effect of Treatment with Berenil Alone and in Combination With Compound III on a 21 Day-old Infection of *Trypanosoma brucei* LUMP 1001

| Pretreatment Day 21 | | Treatment Commencing Day 24 | | No. Cured≠ Out of Total Treated |
|---|---|---|---|---|
| Drug | Dose | Drug | Number and Level of Daily Doses | |
| Berenil | 40 mg./kg. | — | — | 0/10 |
| Berenil | 40 mg./kg. | III | 4 × 20 mg./kg. | 2/10 |
| Berenil | 40 mg./kg. | III | 1 × 80 mg./kg. | 1/9 |
| Berenil + III | 40 mg./kg. 80 mg./kg. | — | — | 0/8 |
| Berenil | 40 mg./kg. | — | — | 0/9 |
| Berenil | 60 mg./kg. | — | — | 0/8 |
| Berenil | 80 mg./kg.* | — | — | 0/8 |
| — | — | III | 4 × 80 mg./kg. | 0/10 |
| Berenil | 40 mg./kg. | III | 4 × 80 mg./kg. | 0/8 |
| Berenil | 60 mg./kg. | III | 4 × 80 mg./kg. | 9/12 |
| Berenil | 80 mg./kg. | III | 4 × 80 mg./kg. | 10/10 |

≠ Cure indicates that relapses did not occur, i.e., that there was a complete absence of parasites in the blood for at least 90 days after treatment or until the end of the experiment.
*Given as 2 × 40 mg./kg. on day 21 and day 24.

The initial results with the three Compounds I, II and III tested against early infections (3 day) of *T. brucei* TREU 667/1 showed trypanocidal action in II only at the high level of 4×20 mg./kg., a little in Compound III at the low level 4×5 mg./kg. and a very definite therapeutic action at the higher level of 4×20 mg./kg. Compound I at the dose levels used, was completely ineffective.

Because of these results, a further group of mice were tested at a higher level (4×80 mg./kg.) with Compound II, and the drug at this level cured an early infection.

Experiments using the most promising of the drugs, Compound III, against an established (21 day) infection of *T. brucei* TREU 667/1, showed that even administration of 4 doses at 80 mg./kg. failed to permanently cure the infection, although the last of the mice did not relapse for a period of 42 days after treatment.

Various combinations of Compounds II and III also failed to cure the infection (Table 2).

These results indicate that pre-treatment with Berenil followed by the Compound III, results in a permanent cure in 90–100% of mice which have a long-established infection of *T. brucei*, whereas when Berenil is used alone, usually less than 10% would be free of infection.

It is the combination of the drugs, Berenil plus Compound III which is effective, as neither drug on its own has the same effect. A proportion of mice infected for 21 days with *T. brucei* TREU 667/1 and first treated with Berenil alone (40 mg./kg.) and retreated every 30 days, i.e., before any signs of relapse, for a total of 5 months, have been shown to eventually become parasitaemic again. It is also not entirely due to the concentration of the initial dose of Berenil as 21 day old *T. brucei* TREU 667/1 infections have relapsed after treatment even with 160 mg./kg. Berenil (given subcutaneously); but it is important as it requires a higher level of pre-treatment with Berenil (60 and 80 mg./kg.) in the case of *T. brucei* LUMP 1001 than the *T. Brucei* TREU 667/1 to effect a permanent cure. In addition, it would appear that it is not just a question of removal of the mass of trypanosomes circulating in the bloodstream prior to treatment with Compound III, as 5 mg./kg. Berenil will clear all circulating trypanosomes from the bloodstream for up to 20 days (Table 4) and indeed early infections of *T. brucei* TREU 667/1 can be permanently cured at this dose level.

The Compound III could be administered as a single injection rather than in 4 divided doses, and it could also be administered along with the Berenil. This possibility of having a single injection has important practical implications in the treatment of herds of cattle under local African conditions, and would obviate the necessity of continually gathering and treating range cattle.

However, in instances where the dosage of Berenil required was high as against *T. brucei* LUMP 1001, then the effectiveness of dividing the Berenil dose would circumvent the possibility of toxic reactions in the host. In human trypanosomiasis where the consideration of repeated daily treatment is not a major consideration then both the Berenil and Compound III could be given in divided doses. For treatment of trypanosomiasis in humans (Apted, *In 'The African Trypanosomiases' Ed. H. W. Mulligan, George Allen and Unwin, London,* 1970.) Berenil is usually given every day for 7–10 days at a dose rate of 2 mg./kg., and indeed can be given orally (Bailey, *Trans. Roy. Soc. Trop. Med. Hyg.,* 62, 122, 1968).

The effect of pretreatment with other trypanocidal drugs indicates that some of the mice treated with the prophylactic drugs Prothidium and Samorin did not show signs of relapse until 6–7 months after the treatment, and the combined treatment was more effective than the single pretreatment.

The compositions of this invention have particular value in the control of trypanosomiasis in domesticated animals, particularly cattle. For this purpose, they may be administered in unit dosage forms such as boluses, drenches and preferably by injection. The amount of the composition required for treatment of relapsing trypanosomiasis varies in accordance with such factors as the particular composition employed, the species of animal to be treated, the species of infecting parasite and the severity of infection. In general, the compositions of the present invention comprising Berenil and a substituted nitroimidazole when administered by injection to domestic animals in daily doses of from about 5 mg. to about 100 mg. of Berenil and about 10 mg. to 800 mg. of the nitroimidazole per kilogram of animal body weight are highly effective in treating relapsing trypanosomiasis without intolerable toxic effect. When these compounds are to be employed as therapeutic agents, good results are obtained when the animals are injected with a dose of from about 10 mg. to about 80 mg. of Berenil and about 20 mg. to about 320 mg. of the nitroimidazole and preferably 2 mg. to 50 mg. per kilogram of body weight of Berenil and a dose of 20 mg. to 160 mg. of the nitroimidazole compound. Administration of the Berenil and the nitroimidazole may be on the same day or with an interval of about three days. Administration may be in a single dose or divided into a plurality of smaller doses over a period of 24 hours or several days. Where prophylactic treatment is desired and the compounds are administered continuously, satisfactory results are obtained when the animals ingest daily dosages of about 0.1 mg. to 100 mg. of the composition per kilogram of body weight. The unit dosage forms may be readily prepared by conventional formulating techniques and are particularly useful when administration is to be made in a single dose or divided doses over a period of 24 hours.

The exact amount of active ingredient to be employed in the above compositions may vary provided that a sufficient amount is ingested to give the required dosage. In general, tablets, boluses, drenches and intraperitoneal injections containing from about 5 to 70 percent weight of active ingredient may be satisfactorily employed to supply the desired dosage.

When Berenil and the substituted nitroimidazoles of this invention are used in the prevention and treatment of human "sleeping sickness", the compounds can be administered as intravenous, or intraperitoneal injections. The compounds are suspended or dissolved in an inert non-toxic pharmaceutically acceptable carrier and administered. When used as a prophylactic, 2–12 mg./kg. of body weight are injected every 1–8 months. Certain of the nitroimidazole compounds can also be used orally or intraperitoneally against Chagas' disease which is caused by *Trypanosoma cruzi*. The oral dosage is 50–250 mg. per kilogram twice a day for 5–10 days.

When the novel compositions of the present invention are used therapeutically to treat well established infections of trypanosomiasis, a preferred method of treatment is to administer Berenil at a dose range of about 2 mg. to about 50 mg. per kilogram of body weight and 20 mg. to 160 mg. per kilogram of body weight of the nitroimidazole administered concomitantly.

What is claimed is:

1. A composition useful for treating trypanosomiasis in humans and animals caused by *Trypanosoma brucei* TREU 667/1 which comprises 40 mg of diminozene aceturate and 80 'mg of 3'-(1-methyl-5-nitroimidazole-2-yl)-4,5'-hexamethylene-$\Delta^2$-isoxazoline.

2. A method for the treatment of trypanosomiasis in humans and animals caused by *Trypanosoma brucei* TREU 667/1 which comprises administering 40 mg per kilogram of body weight of berenil aceturate and
   (a) at the same time, administering 80 mg per kilogram of body weight of 3'-(1-methyl-5-nitroimidazolyl-2-yl)4',5'-hexamethylene-$\Delta^2$-isoxazoline; or
   (b) 3 days after the berenil aceturate treatment, commencing treatment with a single dose of 80 mg per kilogram of body weight, or 4 daily divided doses of 20 mg per kilogram of body weight of 3'-(1-methyl-5-nitroimidazolyl-2-yl)-4',5'-hexamethylene-$\Delta^2$-isoxazoline.

3. A method for the treatment of trypanosomiasis in humans and animals caused by *Trypanosoma brucei* LUMP 1001 which comprises:
   (a) administering 60 to 80 mg per kilogram of body weight of berenil aceturate; and
   (b) 3 days after the berenil aceturate treatment, commencing treatment with 4 daily divided doses of 80 mg per kilogram of body weight of 3'-(1-methyl-5-nitroimidazolyl-2-yl)4',5'-hexamethylene-66 $^2$-isoxazoline.

* * * * *